United States Patent [19]

Gentry et al.

[11] Patent Number: 5,399,751
[45] Date of Patent: Mar. 21, 1995

[54] METHOD FOR RECOVERING CARBOXYLIC ACIDS FROM AQUEOUS SOLUTIONS

[75] Inventors: Joseph C. Gentry, Dallas, Tex.; John C. McIntyre, Hackettstown, N.J.; Timothy L. Holmes, Kingwood; Ronald G. Gualy, Dallas, both of Tex.

[73] Assignee: Glitsch, Inc., Dallas, Tex.

[21] Appl. No.: 147,394

[22] Filed: Nov. 5, 1993

[51] Int. Cl.⁶ ............................................. C07C 51/42
[52] U.S. Cl. .................................... 562/608; 203/15; 203/16; 203/51; 203/60; 203/61
[58] Field of Search ............... 562/608; 203/60, 15, 203/16, 51, 61

[56] References Cited

U.S. PATENT DOCUMENTS

| | | | |
|---|---|---|---|
| 1,839,932 | 1/1932 | Ricard et al. | 562/608 |
| 2,028,800 | 1/1936 | Othmer | 202/42 |
| 2,033,978 | 3/1936 | Dreyfus | 260/122 |
| 2,048,441 | 8/1936 | Gordon | 202/42 |
| 2,159,146 | 5/1939 | Guinot | 202/42 |
| 2,526,508 | 10/1950 | Scheeline et al. | 260/540 |
| 2,574,256 | 11/1951 | Flisik et al. | 558/443 |
| 2,588,268 | 3/1952 | Mercer et al. | 202/42 |
| 3,040,094 | 6/1962 | Stine et al. | 260/527 |
| 3,394,058 | 7/1968 | Hohenschutz et al. | 203/60 |
| 3,470,238 | 9/1969 | Asano | 560/205 |
| 3,816,524 | 6/1974 | Grimstead | 260/527 R |
| 4,353,784 | 10/1982 | Koga et al. | 203/16 |
| 4,405,717 | 9/1983 | Urbas | 435/140 |
| 4,551,208 | 11/1985 | Bott et al. | 203/60 |
| 4,672,219 | 6/1987 | Iwabuchi et al. | 250/578 |
| 4,729,818 | 3/1988 | Berg | 203/16 |
| 4,735,690 | 4/1988 | Berg et al. | 203/51 |
| 4,786,370 | 11/1988 | Berg | 203/15 |
| 4,877,490 | 10/1989 | Berg et al. | 203/15 |
| 4,909,907 | 3/1990 | Berg | 203/51 |
| 4,935,100 | 6/1990 | Berg et al. | 203/15 |
| 5,006,205 | 4/1991 | Berg et al. | 203/15 |
| 5,160,412 | 11/1992 | Berg | 203/16 |
| 5,167,774 | 12/1992 | Berg | 203/16 |
| 5,173,156 | 12/1992 | Berg et al. | 203/15 |
| 5,175,357 | 12/1992 | Van Brunt | 562/513 |
| 5,227,029 | 7/1993 | Berg et al. | 203/51 |

OTHER PUBLICATIONS

American Cyanamid Company, "Organo-phosphines," Technical bulletin (Feb. 1990).
American Cyanamid Company, "CYANEX®Extractants," Technical bulletin (Mar. 1991).
American Cyanamid Company, "Solvent Extraction Reagent", Technical bulletin (Apr. 1991).
American Cyanamid Company, "The Recovery of Mineral Acids With CYANTEX®923 Extractant," Technical Bulletin No. 89-01 (1992).
Rickelton, W. A. and Boyle, R. J. "Solvent Extraction With Organophosphines -Commerical & Potential Applications," Cyanamid Canada Inc. (1993).
Robbins, Larry A., Ph.D., "Liquid-Liquid Extraction," Perry's *Chemical Engineers' Handbook* 6th Edition, Section 15, 1-19 (1984).

(List continued on next page.)

*Primary Examiner*—Arthur C. Prescott
*Attorney, Agent, or Firm*—Johnson & Wortley

[57] ABSTRACT

Disclosed is a method for recovering carboxylic acids having from one to ten carbon atoms, and particularly formic acid, acetic acid and mixtures of formic and acetic acids, from aqueous solutions, in which the aqueous solution is contacted with solvent consisting essentially of mixed trialkylphosphine oxides in counter-current liquid-liquid extraction flow in a contacting step to thereby transfer the acids from the aqueous solution to the solvent, thus producing a raffinate relatively low in acid content and a rich solvent. The rich solvent is preferably dehydrated to separate water therefrom and yield a dehydrated rich solvent. The dehydrated rich solvent then has the acids stripped from it and the resulting lean solvent is then returned to the liquid-liquid extraction step, while the separated acids are split into their constituent components in a distillation operation.

63 Claims, 2 Drawing Sheets

METHOD FOR RECOVERING CARBOXYLIC ACIDS FROM AQUEOUS SOLUTIONS

This invention relates to methods for recovering carboxylic acids having from one to ten carbon atoms, and particularly formic acid, acetic acid, and mixtures of formic and acetic acids from aqueous solutions containing the same.

BACKGROUND OF THE INVENTION

A number of industrially significant processes produce as a waste product dilute solutions of short chain carboxylic acids, particularly formic acid and acetic acid. Typically these solutions are in the range of one to three percent acid by weight. Heretofore it has been common to discard such solutions to the environment, but present day concerns about pollution are increasingly making it necessary to clean such waste water solutions and/or to recover the acids that they contain as economically valuable byproducts of the processes.

Conventional recovery systems, such as distillation, or extractive distillation, tend to be objectionably energy intensive and uneconomical, as well as involving process difficulties such as the formation of azeotropes and difficult-to-break emulsions and the like.

There is thus a need for a method of treating waste water containing short chain carboxylic acids in a manner which will produce a waste water product which needs little or no after treatment before its ultimate discharge or reuse as process water in a plant, and which produces recovered carboxylic acids of such purity and quality as to be saleable or reusable in a process plant, in an economical manner. The present invention is designed to fill that need.

SUMMARY OF THE INVENTION

Broadly considered, in accordance with the present invention, there is provided a method for recovering short chain carboxylic acids having from one to ten carbon atoms, and particularly formic acid and acetic acid and mixtures thereof from dilute aqueous solutions of such acids. Typical concentrations of aqueous solutions amenable to treatment by the method of the invention are one to three percent by weight acids. In accordance with the invention, the aqueous solution is brought into liquid-liquid contact with a water immiscible high boiling trialkylphosphine oxide mixture extractant, and the acids are largely absorbed into the extractant, leaving a substantially pure water raffinate, which is then passed to further treatment, disposal or reuse. The solvent extractant, now rich in acids, is then preferably dehydrated, and the water stream resulting therefrom is preferably recycled to the incoming aqueous solution. The rich solvent is then stripped of its dissolved acids in a distillation process, and the now lean extractant solvent is returned to the liquid-liquid extraction process. If needed, the removed acids are then split into components which are essentially single species of desired purity by distillation, and are thus marketable products or products usable within a plant for other processes.

The preferred solvent extractant for use in the invention is a mixture of four trialkylphosphine oxides, manufactured by Cytech Industries under the trademark CYANEX 923.

The preferred solvent extractant is a mixture of four trialkylphosphine oxides as follows:

| $R_3P(O)$ $R_2R'P(O)$ $RR_2'P(O)$ $R_3'P(O)$ |
|---|
| Where R = $[CH_3(CH_2)_7]$ - normal octyl |
| R' = $[CH_3(CH_2)_5]$ - normal hexyl |
| Average Molecular Weight = 348 (approximately) |

Typical properties of this solvent are reported as follows:

| | |
|---|---|
| Trialkylphosphine oxides | 93% |
| Appearance | Colorless mobile liquid |
| Specific Gravity | 0.88 at 23° C. |
| Freezing Point | −5 to 0° C. |
| Viscosity | 40.0 centipoise at 25° C. |
| | 13.7 centipoise at 30°C. |
| Flashpoint | 182° C. |
| (Closed Cup Setaflash) | |
| Autoignition Temperature | 218° C. |
| Vapor Pressure | 0.09 mm Hg at 31° C. |
| Boiling Point | 310° C. at 50 mm Hg |
| Solubility in Water | 10 mg/l |
| Solubility of Water in CYANEX 923 extractant | 8 w/o |

When in this specification and in the accompanying claims the term 'solvent consisting essentially of mixed trialkylphosphine oxides' is used, the material referred to is that just described and characterized above, and its equivalents.

In accordance with the present invention, a method for recovering carboxylic acids having from one to ten carbon atoms and particularly acetic acid and formic acid from aqueous solutions containing mixtures thereof is provided which includes contacting the aqueous solution with a solvent consisting essentially of mixed trialkylphosphine oxides in counter current liquid-liquid extraction flow in a contacting step to thereby transfer acids from the aqueous solution to said solvent. This extraction produces a raffinate relatively low in acid content and a solvent relatively rich in acid content, although the acid-rich solvent contains some water. It is dehydrated by applying heat thereto to separate water therefrom in a dehydration step, thereby producing a water stream and a dehydrated rich solvent stream. The acids are stripped from the dehydrated rich solvent stream in a stripping step by applying heat thereto to produce a recycle solvent consisting essentially of mixed trialkylphosphine oxides for recycle to the liquid-liquid extraction flow described above and an acid stream. When the acid stream contains more than one acid, it is split into its constituent acids in a splitting step by distillation.

Preferably, the recycle solvent consisting essentially of mixed trialkylphosphine oxides is recycled to said contacting step, and the water stream from dehydration of the rich solvent is recycled to the incoming aqueous solution.

In further accordance with the invention, the volume ratio of solvent consisting essentially of mixed trialkylphosphine oxides to aqueous solution during said contacting is from about one part solvent to two parts aqueous solution to about two pans solvent to one part aqueous solution. The initial concentration of acids in said aqueous solution is preferably from about one-half percent (0.5%) by weight to about fifteen percent (15%) by weight, although it may be from about one percent (1%) by weight to about ten percent (10%) by weight. It is also preferred that the recycle solvent consisting essentially of mixed trialkylphosphine oxides have an acid content less than about 0.5% by weight.

The contacting of aqueous solution with solvent consisting essentially of mixed trialkylphosphine oxides is performed at a temperature between about 35° C. and about 90° C., and more preferably at a temperature between about 50° C. and about 80° C. Further, the dehydrating step is preferably performed at a pressure of about 200 millimeters of mercury absolute. It is preferred that the stripping be performed at a temperature of from about 250° C. to about 300° C. at the hottest region of said stripping step, and it is also preferred that the stripping be performed at a pressure of from about 15 to about 50 millimeters of mercury absolute. The pressure at which said stripping is performed is desirably sufficient to avoid freezing of any acid, particularly acetic acid, during said stripping or downstream thereof.

In order to maximize energy efficiency, heat in the recycle solvent consisting essentially of mixed trialkylphosphine oxides from the stripping step may be transferred at least in part to the rich solvent in the dehydration step. Also, heat in the recycle solvent consisting essentially of mixed trialkylphosphine oxides from the stripping step may be transferred at least in part to the acid stream being split into constituent acids.

Fresh solvent consisting essentially of mixed trialkylphosphine oxides for use in the process may be purified prior to being contacted with said aqueous solution, for example by water washing or by distillation.

Although several modes of operation are possible, it is preferred that the contacting be effected by dispersing the solvent consisting essentially of mixed trialkylphosphine oxides as a dispersed phase in the aqueous solution which is then the continuous phase.

Vapors vented from the dehydration and/or said stripping steps may be scrubbed with scrubbing solvent consisting essentially of mixed trialkylphosphine oxides employed in the contacting step, and acids thereby dissolved in the scrubbing solvent may thereafter be recovered therefrom.

Any solvent consisting essentially of mixed trialkylphosphine oxides which becomes entrained in the raffinate from the contacting step may be coalesced out of the raffinate, thus increasing raffinate purity and recovering solvent for reuse.

Undesirable water in the final acid products may be reduced or eliminated by providing a side stream which is drawn from the distillation splitting step at a region where the water concentration therein is greatest, or at a region where an azeotrope is formed between water and formic acid in the course of being distilled.

Impurities in the incoming aqueous solution which may interfere with the process may be eliminated by a pretreatment in which rich solvent from the contacting step is mixed with incoming aqueous solution prior to its delivery to the contacting step and then the rich solvent and aqueous solution are separated from each other by coalescing the rich solvent from said aqueous solution, with the separated aqueous solution then being delivered to the contacting step and the separated rich solvent being delivered to the dehydration step.

Impurities tending to accumulate in the recycle solvent consisting essentially of mixed trialkylphosphine oxides may be removed therefrom as it is in the course of being recycled. These impurities may be removed by vacuum distillation of at least a portion of the solvent, or by activated carbon filtration of at least a portion of the solvent, or by contacting at least a portion of the solvent with an ion exchange agent in the course of its being recycled. Also, the impurities may be removed by neutralization with a basic additive of at least a portion of the solvent for recycle in the course of its being recycled. The impurities may also be controlled by adjusting the relative flow rates of aqueous solution and recycle solvent consisting essentially of mixed trialkylphosphine oxides so that the equilibrium concentrations of impurities in the solvent and in the raffinate are each at acceptable levels.

DETAILED DESCRIPTION OF THE PREFERRED EMBODIMENTS

Figure 1:
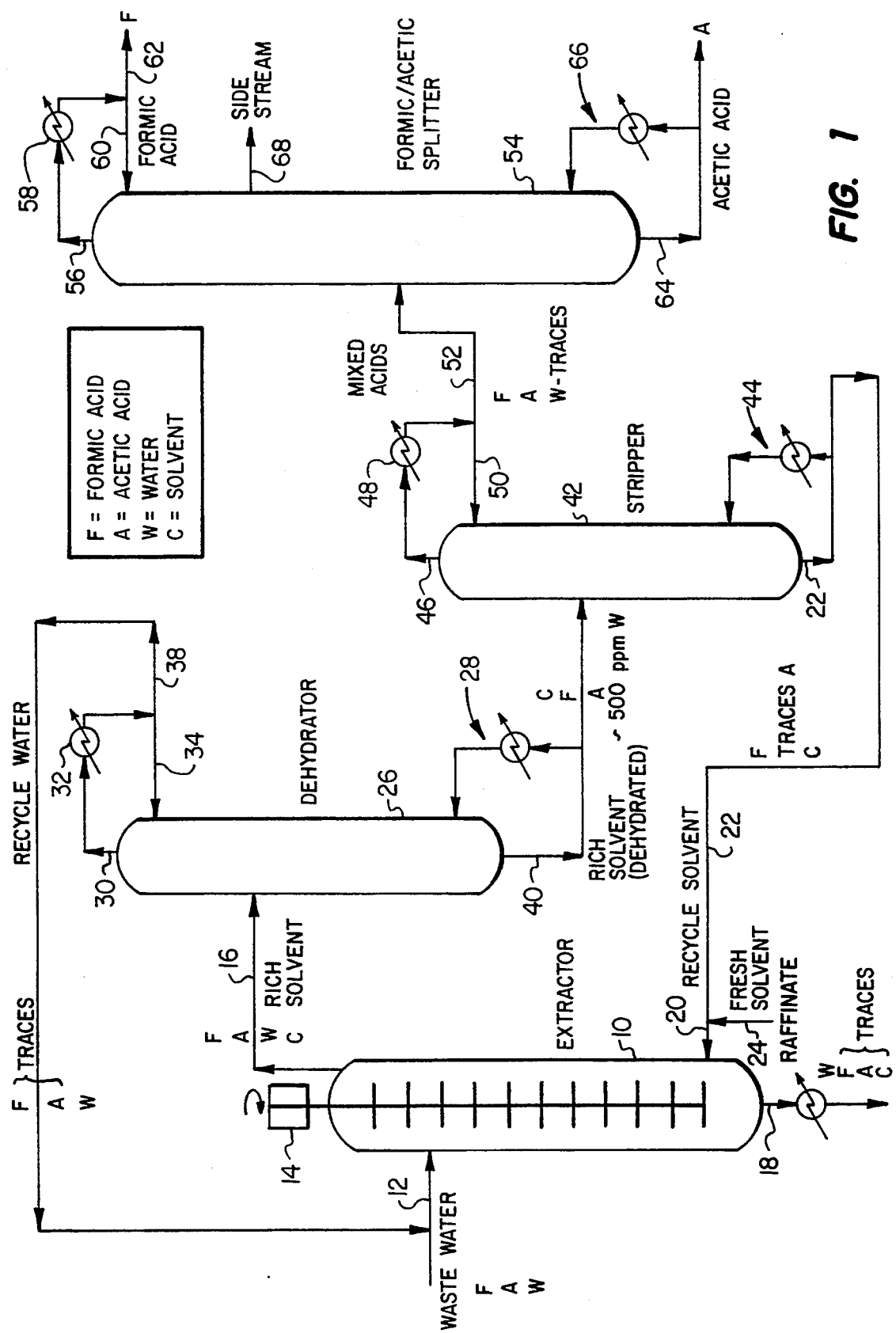
FIG. 1 is a diagrammatic flowsheet for a plant for practicing the method of the invention, the plant being fitted particularly for recovering and separating formic acid and acetic acid from a dilute aqueous solution.

Attention is first directed to FIG. 1 which shows in simplified flow diagram form a plant arranged for the practice of the method of the invention. Aqueous solution or waste water containing the acids sought to be recovered is delivered to extractor 10 through input line 12. The extractor is shown as being of the rotating plate type, with a motor 14 provided to rotate the plates. Various other kinds of liquid-liquid extractor devices may be employed. The top stream out of the extractor 10 is a rich solvent stream that leaves the extractor through line 16, while the bottom stream is a raffinate leaving through line 18. Fresh solvent and recycle solvent are introduced into the extractor 10 near the bottom through line 20, the recycle solvent being delivered to line 20 through line 22 and fresh solvent, when needed, being delivered through line 24. The volume ratio of solvent and aqueous solution fed to the extractor is preferably between about one-to-two and two-to-one. The initial concentration of acids in the aqueous solution feed is from about 0.5% to about 15%, and preferably from about 1% to about 6% by weight. The operational temperature in the contacting step is between about 35° C. and about 90° C., and preferably between about 50° C. and about 80° C. The phase separation line is preferably at the top region of the extractor, and the dispersed phase is the solvent while the continuous phase is the aqueous solution.

The rich acid containing solvent is delivered through line 16 to dehydrator 26. Heat is input to the dehydrator through a reboiler system 28 and water exits the dehydrator at the top through line 30, which is provided with a condenser 32 and reflux line 34 if desired. The water stream is delivered through line 38 in a recycle circuit back to input line 12. Alternately, the water stream may be delivered out of the plant for use or disposition elsewhere or combined with the raffinate stream. The pressure in the dehydrator is preferably about 200 millimeters of mercury absolute.

Rich solvent leaves the dehydrator through line 40 which delivers it to stripper 42. In stripper 42, the acids are separated from the solvent and through application of heat through reboiler system 44, and the mixed acids exit the stripper at the top through line 46, which is provided with a condenser 48 and a recycle line 50. The mixed acids are delivered through line 52 to splitter 54. The stripped solvent leaves the bottom of stripper 42 through line 22 and is recycled to the extractor 10. The acid content of the stripped solvent for recycle is less than about 0.5% by weight. At the hottest region of the stripper, the operating temperature is from about 250° C. to about 300° C., and the pressure in the stripper is from about 15 to about 50 millimeters of mercury absolute. In any event, the stripping pressure should be such as to avoid freezing of any acids there or downstream. If desired, part of the heat in the stripped solvent may be heat exchanged with rich solvent at the dehydrator reboiler system 28, and also, if desired, pan of the heat in the stripped solvent may be heat exchanged with the bottom acid stream in reboiler system 66 discussed below.

The mixed acids delivered to splitter 54 through line 52 are separated in a distillation process, with formic acid exiting the splitter through line 56 and being condensed in condenser 58 and refluxed in part through line 60 with the balance being delivered out of the plant through product line 62. The acetic acid is delivered out of the bottom of the unit through line 64, and a reboiler system 66 is provided to deliver heat energy into the distillation tower or splitter 54. In accordance with the invention, a side stream 68 may be taken off the splitter at a point where the concentration of any water contaminant is at its highest; this point most usually being at a point where an azeotrope is formed between water and the lighter acid, that is, the formic acid.

Figure 2:
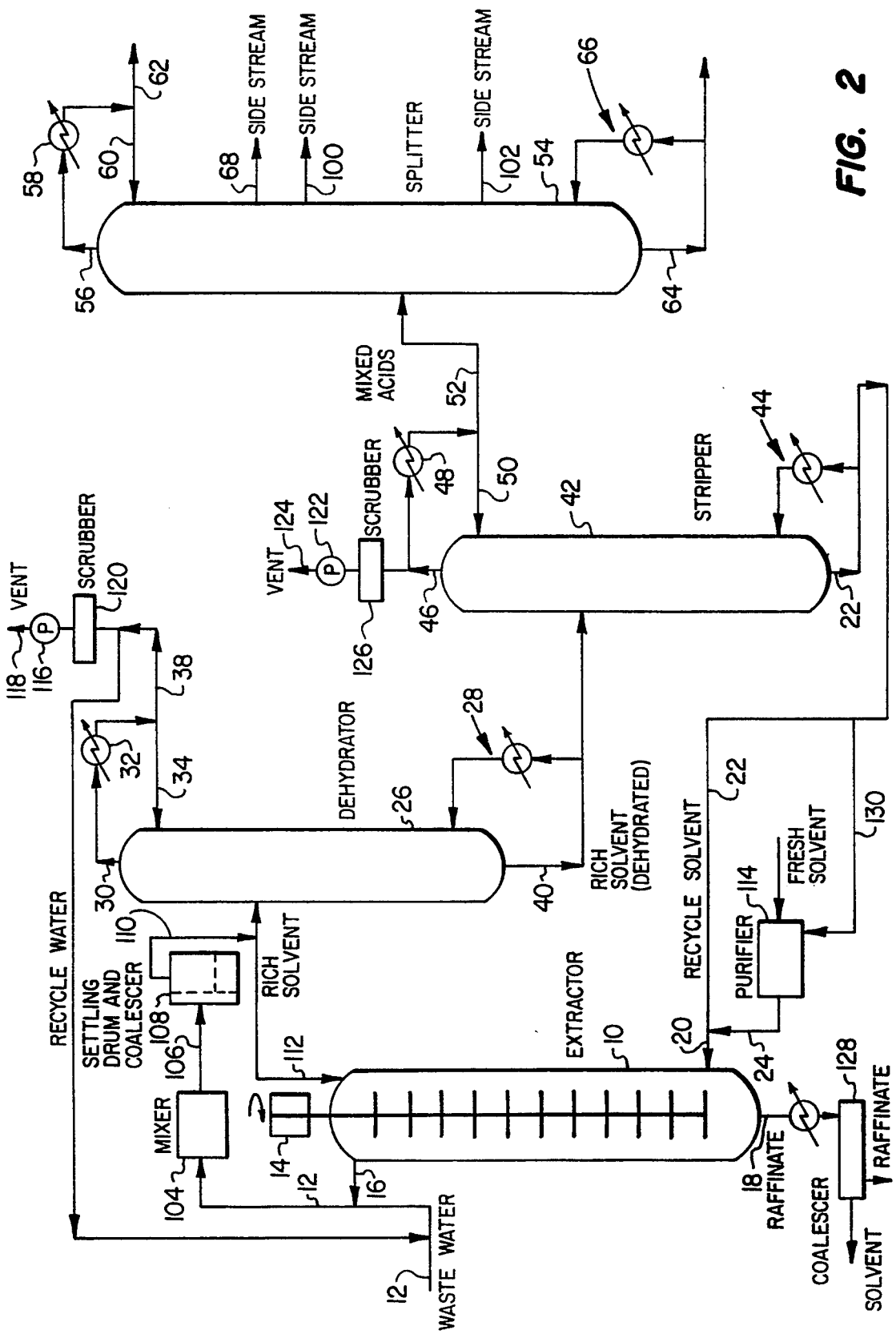
FIG. 2 is a diagrammatic flowsheet for a plant for practicing the method of the invention to recover and separate a mixture of short chain carboxylic acids, and showing certain method features which may also be employed in the plant and method of FIG. 1.

Attention is now directed to FIG. 2 which is a diagrammatic flow sheet for a plant for practicing other embodiments of the invention. In FIG. 2, pieces of equipment and lines which are identical to those in FIG. 1 are given the same reference characters, and the description of those pans given in connection with FIG. 1 applies to the plant shown in FIG. 2 also.

The plant shown in FIG. 2 differs from that of FIG. 1 in that it is designed to process an aqueous solution containing more than formic acid and acetic acid from the group of carboxylic acids having from one to five carbon atoms. Thus the splitter or distillation column 54 in FIG. 2 is provided with additional side stream take-offs 100 and 102 for recovering additional acids beyond those which the distillation operation will tend to separate to the top and bottom of that tower. Those skilled in the art will appreciate that the separation of the recovered mixed acids may be effected stage-wise in a series of towers rather than in a single tower, if desired.

It has been discovered that impurities in the waste water or input aqueous solution entering the system through fine 12 may cause operational difficulties through inducing emulsification in various streams in the plant, and as well as other operating inefficiencies. In accordance with the invention, these impurities may be eliminated by an additional process step in which rich solvent leaving extractor 10 through line 16 is joined with fresh incoming aqueous solution in line 12 and these materials are passed to mixer 104. After being thoroughly mixed, the rich solvent and the incoming aqueous solution pass through line 106 to a coalescer 108 where the species separate, and rich solvent then passes through line 110 to the dehydrator 26, while acid containing water is fed through line 112 into extractor 10. In this manner, the impurities in the incoming aqueous solution are made more readily coalescible.

It has also been found that unexpected impurities may be in the fresh solvent which is charged to the plant at startup, or which is added to the plant in the course of operations. As appears in FIG. 2, a purifier 114 may be placed in the fresh solvent input line 24 to remove these impurities. The purifier 114 may be a distillation tower, an activated carbon bed, an ion exchange system, a water wash system, or other separating equipment. Since the problem of impurities in the fresh solvent is most acute at startup, piping may be provided to utilize equipment of the plant during startup to effect the removal of the impurities in the fresh solvent. For example, stripper 42 or dehydrator 26 may be temporarily so employed during startup. Additionally, the impurities may be removed in a purifier which is a separate stand-alone plant, if desired.

As has been explained above, it is preferred that dehydrator 26 and stripper 42 be operated at vacuum. The vacuum inducing equipment is shown in FIG. 2, although it should be understood that similar equipment would be present in a plant arranged as in FIG. 1. This equipment includes pump 116 and vent 118 in line 38 out of the top of the dehydrator 26. The pump may be a mechanical pump or other vacuum inducing equipment such as a steam ejector. Since the stream through vent 118 may contain some acids and other material which would be viewed as pollutants, a scrubber 120 may be provided. Scrubber 120 may use as the scrubbing fluid the same kind of solvent as is employed in the plant as the main extractant, and the solvent may be passed through scrubber 120 as a side loop in the main solvent circuit of the plant.

Similarly for tower 42, a vacuum pump 122 and vent 124 are provided. Also, a scrubber 126 is provided for removing this acid and other pollutants from the stream leaving the plant through vent 124.

As has been noted above, impurities may tend to accumulate in the solvent as it is cycled through the process. These impurities may be conveniently removed from the recycle solvent passing through line 22, by drawing off at least a portion of the recycle solvent through line 130 and passing it through purifier 114, or through a separate purifier, where the impurities may be removed by vacuum distillation, activated carbon filtration, ion exchange, or neutralization with a basic additive, or otherwise.

Under some operating conditions, the raffinate leaving the extractor 10 through line 18 may have some solvent physically entrained in it. This solvent can be removed and recovered, for example in a coalescer 128. The recovered solvent may be returned to the main solvent circuit of the plant, and the raffinate, now freed of entrained solvent may be discarded, further processed, or reused in the plant.

Various features of the plant illustrated in FIG. 2 which is designed for processing multiple acids in the incoming aqueous solution stream may be incorporated into the plant shown in FIG. 1, which is designed for processing formic acid and acetic acid only, and the converse is the case as will be appreciated by those skilled in the art.

What is claimed is:

1. A method for recovering acetic acid and formic acid from an aqueous solution thereof comprising:
   contacting said aqueous solution with solvent consisting essentially of mixed trialkylphosphine oxides in counter-current liquid-liquid extraction flow in a contacting step to thereby transfer acetic acid and formic acid from said aqueous solution to said solvent, thereby producing a raffinate relatively low in acid content and a solvent relatively rich in acid content, said acid-rich solvent containing some water;

dehydrating said rich solvent by applying heat thereto to separate water therefrom in a dehydration step thereby producing a water stream and a dehydrated rich solvent stream;

stripping the acetic acid and formic acid from said dehydrated rich recycle solvent stream in a stripping step by applying heat thereto to produce a solvent consisting essentially of mixed trialkylphosphine oxides for recycle to said liquid-liquid extraction flow, and an acid stream containing acetic acid and formic acid; and splitting said acid stream into acetic acid and formic acid in a splitting step by distillation.

2. A method in accordance with claim 1 in which said recycle solvent consisting essentially of mixed trialkylphosphine oxides is recycled to said contacting step.

3. A method in accordance with claim 1 in which said water stream from dehydration of said rich solvent is recycled to said aqueous solution.

4. A method in accordance with claim 1 in which the volume ratio of solvent consisting essentially of mixed trialkylphosphine oxides to aqueous solution during said contacting is from about one part solvent to two parts aqueous solution to about two parts solvent to one part aqueous solution.

5. A method in accordance with claim 1 in which the initial concentration of acids in said aqueous solution is from about one percent (1%) by weight to about six percent (6%) by weight.

6. A method in accordance with claim 1 in which the initial concentration of acids in said aqueous solution is from about one-half percent (0.5%) by weight to about fifteen percent (15%) by weight.

7. A method in accordance with claim 1 in which said recycle solvent consisting essentially of mixed trialkylphosphine oxides has an acid content less than about 0.5% by weight.

8. A method in accordance with claim 1 in which said contacting of aqueous solution with solvent consisting essentially of mixed trialkylphosphine oxides is performed at a temperature between about 35° C. and about 90° C.

9. A method in accordance with claim 1 in which said contacting of aqueous solution with solvent consisting essentially of mixed trialkylphosphine oxides is performed at a temperature between about 50° C. and about 80° C.

10. A method in accordance with claim i in which said dehydrating step is performed at a pressure of about 200 millimeters of mercury absolute.

11. A method in accordance with claim 1 in which said stripping is performed at a temperature of from about 250° C. to about 300° C. at the hottest region of said stripping step.

12. A method in accordance with claim 1 in which said stripping is performed at a pressure of from about 15 to about 50 millimeters of mercury absolute.

13. A method in accordance with claim 12 in which the temperature and pressure at which said stripping is performed is sufficient to avoid freezing of said acetic acid during said stripping or downstream thereof.

14. A method in accordance with claim 1 in which heat in said recycle solvent consisting essentially of mixed trialkylphosphine oxides from said stripping step is transferred at least in part to said rich solvent in said dehydration step.

15. A method in accordance with claim 1 in which heat in said recycle solvent consisting essentially of mixed trialkylphosphine oxides from said stripping step is transferred at least in part to said acid stream being split into acetic acid and formic acid.

16. A method in accordance with claim 1 in which said contacting is effected by dispersing said solvent consisting essentially of mixed trialkylphosphine oxides as a dispersed phase in said aqueous solution as a continuous phase.

17. A method in accordance with claim 1 in which fresh solvent consisting essentially of mixed trialkylphosphine oxides is purified prior to being contacted with said aqueous solution.

18. A method in accordance with claim 17 in which fresh solvent consisting essentially of mixed trialkylphosphine oxides is purified by water washing.

19. A method in accordance with claim 17 in which fresh solvent consisting essentially of mixed trialkylphosphine oxides is purified by distillation.

20. A method in accordance with claim 1 in which vapors vented from said dehydration and/or said stripping steps are scrubbed with scrubbing solvent consisting essentially of mixed trialkylphosphine oxides employed in said contacting step.

21. A method in accordance with claim 1 in which vapors vented from said dehydration and/or said stripping steps are scrubbed with scrubbing solvent consisting essentially of mixed trialkylphosphine oxides, and acids thereby dissolved in said scrubbing solvent are thereafter recovered therefrom.

22. A method in accordance with claim 1 in which any solvent consisting essentially of mixed trialkylphosphine oxides entrained in said raffinate from said contacting step is coalesced out of said raffinate.

23. A method in accordance with claim 1 in which a side stream is drawn from said distillation splitting step at a region where the water concentration therein is greatest.

24. A method in accordance with claim 1 in which a side stream is drawn from said distillation splitting step at a region where an azeotrope is formed between water and formic acid in the course of being distilled.

25. A method in accordance with claim 1 in which rich solvent from said contacting step is mixed with said aqueous solution prior to its delivery to said contacting step and then said rich solvent and aqueous solution are separated from each other by coalescing said rich solvent from said aqueous solution, with said separated aqueous solution being delivered to said contacting step and said separated rich solvent being delivered to said dehydration step.

26. A method in accordance with claim 2 in which impurities tending to accumulate in said recycle solvent consisting essentially of mixed trialkylphosphine oxides are removed therefrom in the course of its being recycled.

27. A method in accordance with claim 26 in which said impurities are removed by vacuum distillation of at least a portion of said recycle solvent consisting essentially of mixed trialkylphosphine oxides in the course of its being recycled.

28. A method in accordance with claim 26 in which said impurities are removed by activated carbon filtration of at least a portion of said recycle solvent consisting essentially of mixed trialkylphosphine oxides in the course of its being recycled.

29. A method in accordance with claim 26 in which said impurities are removed by contacting at least a portion of said recycle solvent consisting essentially of mixed trialkylphosphine oxides with an ion exchange agent in the course of its being recycled.

30. A method in accordance with claim 26 in which said impurities are removed by neutralization with a basic additive of at least a portion of said recycle solvent consisting essentially of mixed trialkylphosphine oxides in the course of its being recycled.

31. A method in accordance with claim 2 in which said impurities are controlled by adjusting the relative flow rates of aqueous solution and recycle solvent consisting essentially of mixed trialkylphosphine oxides so that the equilibrium concentrations of impurities in said solvent consisting essentially of mixed trialkylphosphine oxides for recycle and in said raffinate are each at acceptable levels.

32. A method for recovering carboxylic acids from an aqueous solution containing at least one acid from the group consisting of carboxylic acids having from one to ten carbon atoms comprising:
contacting said aqueous solution with solvent consisting essentially of mixed trialkylphosphine oxides in counter-current liquid-liquid extraction flow in a contacting step to thereby transfer said acids from said aqueous solution to said solvent, thereby producing a raffinate relatively low in acid content and a solvent relatively rich in acid content, said acid-rich solvent containing some water;
dehydrating said rich solvent by applying heat thereto to separate water therefrom in a dehydration step thereby producing a water stream and a dehydrated rich solvent stream; and
stripping the acids from said dehydrated rich solvent stream in a stripping step by applying heat thereto to produce a recycle solvent consisting essentially of mixed trialkylphosphine oxides for recycle to said liquid-liquid extraction flow and an acid stream containing said acids.

33. A method in accordance with claim 32 in which said aqueous solution contains at least two carboxylic acids and further comprising splitting said acid stream into individual acids in a splitting step by distillation.

34. A method in accordance with claim 32 in which said solvent consisting essentially of mixed trialkylphosphine oxides for recycle is recycled to said contacting step.

35. A method in accordance with claim 32 in which said water stream from dehydration of said rich solvent is recycled to said aqueous solution.

36. A method in accordance with claim 32 in which the volume ratio of solvent consisting essentially of mixed trialkylphosphine oxides to aqueous solution during said contacting is from about one part solvent to two parts aqueous solution to about two parts solvent to one part aqueous solution.

37. A method in accordance with claim 32 in which the initial concentration of acids in said aqueous solution is from about one percent (1%) by weight to about six percent (6%) by weight.

38. A method in accordance with claim 32 in which the initial concentration of acids in said aqueous solution is from about one-half percent (0.5%) by weight to about fifteen percent (15%) by weight.

39. A method in accordance with claim 32 in which said solvent consisting essentially of mixed trialkylphosphine oxides for recycle has an acid content less than about 0.5% by weight.

40. A method in accordance with claim 32 in which said contacting of aqueous solution with solvent consisting essentially of mixed trialkylphosphine oxides is performed at a temperature between about 35° C. and about 90° C.

41. A method in accordance with claim 32 in which said contacting of aqueous solution with solvent consisting essentially of mixed trialkylphosphine oxides is performed at a temperature between about 50° C. and about 80° C.

42. A method in accordance with claim 32 in which said dehydrating step is performed at a pressure of about 200 millimeters of mercury absolute.

43. A method in accordance with claim 32 in which said stripping is performed at a temperature of from about 250° C. to about 300° C. at the hottest region of said stripping step.

44. A method in accordance with claim 32 in which said stripping is performed at a pressure of from about 15 to about 50 millimeters of mercury absolute.

45. A method in accordance with claim 44 in which the temperature and pressure at which said stripping is performed is sufficient to avoid freezing of said any acid during said stripping or downstream thereof.

46. A method in accordance with claim 32 in which heat in said recycle solvent consisting essentially of mixed trialkylphosphine oxides from said stripping step is transferred at least in part to said rich solvent in said dehydration step.

47. A method in accordance with claim 32 in which heat in said recycle solvent consisting essentially of mixed trialkylphosphine oxides from said stripping step is transferred at least in part to said acid stream being split into its constituent acids.

48. A method in accordance with claim 32 in which said contacting is effected by dispersing said solvent consisting essentially of mixed trialkylphosphine oxides as a dispersed phase in said aqueous solution as a continuous phase.

49. A method in accordance with claim 32 in which fresh solvent consisting essentially of mixed trialkylphosphine oxides is purified prior to being contacted with said aqueous solution.

50. A method in accordance with claim 49 in which fresh solvent consisting essentially of mixed trialkylphosphine oxides is purified by water washing.

51. A method in accordance with claim 49 in which fresh solvent consisting essentially of mixed trialkylphosphine oxides is purified by distillation.

52. A method in accordance with claim 32 in which vapors vented from said dehydration and/or said stripping steps are scrubbed with scrubbing solvent consisting essentially of mixed trialkylphosphine oxides employed in said contacting step.

53. A method in accordance with claim 32 in which vapors vented from said dehydration and/or said stripping steps are scrubbed with scrubbing solvent consisting essentially of mixed trialkylphosphine oxides, and acids thereby dissolved in said scrubbing solvent are thereafter recovered therefrom.

54. A method in accordance with claim 32 in which any solvent consisting essentially of mixed trialkylphosphine oxides entrained in said raffinate from said contacting step is coalesced out of said raffinate.

55. A method in accordance with claim 32 in which a side stream is drawn from said distillation splitting step at a region where the water concentration therein is greatest.

56. A method in accordance with claim 32 in which a side stream is drawn from said distillation splitting step at a region where an azeotrope is formed between water and formic acid in the course of being distilled.

57. A method in accordance with claim 32 in which rich solvent from said contacting step is mixed with said aqueous solution prior to its delivery to said contacting step and then said rich solvent and aqueous solution are separated from each other by coalescing said rich solvent from said aqueous solution, with said separated aqueous solution being delivered to said contacting step and said separated rich solvent being delivered to said dehydration step.

58. A method in accordance with claim 34 in which impurities tending to accumulate in said recycle solvent consisting essentially of mixed trialkylphosphine oxides are removed therefrom in the course of its being recycled.

59. A method in accordance with claim 58 in which said impurities are removed by vacuum distillation of at least a portion of said recycle solvent consisting essentially of mixed trialkylphosphine oxides in the course of its being recycled.

60. A method in accordance with claim 58 in which said impurities are removed by activated carbon filtration of at least a portion of said recycle solvent consisting essentially of mixed trialkylphosphine oxides in the course of its being recycled.

61. A method in accordance with claim 58 in which said impurities are removed by contacting at least a portion of said solvent consisting essentially of mixed trialkylphosphine oxides for recycle with an ion exchange agent in the course of its being recycled.

62. A method in accordance with claim 58 in which said impurities are removed by neutralization with a basic additive of at least a portion of said solvent consisting essentially of mixed trialkylphosphine oxides for recycle in the course of its being recycled.

63. A method in accordance with claim 34 in which said impurities are controlled by adjusting the relative flow rates of aqueous solution and recycle solvent consisting essentially of mixed trialkylphosphine oxides so that the equilibrium concentrations of impurities in said solvent consisting essentially of mixed trialkylphosphine oxides for recycle and in said raffinate are each at acceptable levels.

* * * * *

UNITED STATES PATENT AND TRADEMARK OFFICE
CERTIFICATE OF CORRECTION

PATENT NO. : 5,399,751

DATED : March 21, 1995

INVENTOR(S) : Gentry et al.

Page 1 of 2

It is certified that error appears in the above-indentified patent and that said Letters Patent is hereby corrected as shown below:

| | |
|---|---|
| Title Page, Page 2, Item [56], *Other Publications, continued,* fourth publication | Delete "*Spear.*" Insert --*Separ.*-- |
| Column 2, line 2 | Delete "$RR_2'P(O)$    $R_3'P(O)$" Insert --$RR'_2P(O)$    $R'_3P(O)$-- |
| Column 2, line 25 | Delete "˜solvent" Insert --"solvent-- |
| Column 2, line 26 | Delete "oxides'" Insert --oxides"-- |
| Column 2, line 62 | Delete "pans" Insert --parts-- |
| Column 5, line 14 | Delete "pan" Insert --part-- |
| Column 5, line 37 | Delete "pans" Insert --parts-- |
| Column 5, line 53 | Delete "fine" Insert --line-- |

UNITED STATES PATENT AND TRADEMARK OFFICE
CERTIFICATE OF CORRECTION

PATENT NO. : 5,399,751
DATED : March 21, 1995
INVENTOR(S) : Gentry et al.

It is certified that error appears in the above-indentified patent and that said Letters Patent is hereby corrected as shown below:

Column 7, line 53      After "claim" delete "i"
                           Insert --1--

Signed and Sealed this

Thirtieth Day of January, 1996

BRUCE LEHMAN

*Attest:*

*Attesting Officer*      *Commissioner of Patents and Trademarks*